(12) United States Patent
Tang et al.

(10) Patent No.: US 6,524,232 B1
(45) Date of Patent: Feb. 25, 2003

(54) METHOD FOR RADIOACTIVE STENT DELIVERY

(75) Inventors: Fuh-Wei Tang, Temecula, CA (US); Ty Tiefeng Hu, Mountain View, CA (US); Jean-Francois Corbett, Toronto (CA)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 188 days.

(21) Appl. No.: 09/746,267

(22) Filed: Dec. 22, 2000

(51) Int. Cl.[7] .............................................. A61M 36/04

(52) U.S. Cl. ......................................................... 600/3

(58) Field of Search .............................. 600/3, 4, 5, 6, 600/7, 8, 9, 10, 11, 12

(56) References Cited

U.S. PATENT DOCUMENTS

| | | | |
|---|---|---|---|
| 5,059,166 A | | 10/1991 | Fischell et al. |
| 5,176,617 A | | 1/1993 | Fischell et al. |
| 5,213,561 A | | 5/1993 | Weinstein et al. |
| 5,707,332 A | | 1/1998 | Weinberger |
| 5,730,698 A | | 3/1998 | Fischell et al. |
| 5,871,436 A | | 2/1999 | Eury |
| 6,099,455 A | | 8/2000 | Columbo et al. |
| 6,146,323 A | * | 11/2000 | Fischell .......................... 600/3 |
| 6,241,719 B1 | * | 6/2001 | Wallace et al. ................. 600/4 |
| 6,309,339 B1 | * | 10/2001 | Ciezki et al. .................... 600/3 |

FOREIGN PATENT DOCUMENTS

| | | |
|---|---|---|
| DE | 5059166 | 10/1991 |

OTHER PUBLICATIONS

Liermann, Prophylactic Endovascular Radiotherapy to Prevent Intimal Hyperplasia after Stent Implantation in Femoropopliteal Arteries . Cardiovasc Interv Radiol, (1994), 12–16, vol. 17.

Waksman, Intracoronary Radiation Before Stent Implantation Inhibits Neointimal Formation in Stented Porcine Coronary Arteries, Circulation, (1995), 1383—86, vol. 92, No. 6.
Fischell, Low–Dose ⊖–Particle Emission From 'Stent' Wire Result in Complete, Localized Inhibition of Smooth Muscle Cell Proliferation, Circulation, (1994), 2956–63, vol. 90, No. 6.
Herhlein, Low–Dose Radioactive Endovascular Stents Prevent Smooth Muscle Cell Proliferation and Neointimal Hyperplasia in Rabbits, Circulation, (1995), 1570—75, vol. 92, No. 6.
Hehrlein, Radioactive Stents, Abstract (no publication data available).
Li, A Novel Brachytherapy Source For Teatment of Coronary Artery Restenoisis, Abstract (no publication data availible).
Martin, Radiation for Peripheral Applications: Technical Aspects, Abstract (no publication data available.
Teirstein, Catheter–Based Radiation Therapy to Inhibit Restenosis Following Coronary Stenting, Abstract (no publication data available).
Fischell, The Radioisotope Stent: Conception and Implementation, Abstract, (no publication data available).
Alexander,Thomas. "Vascular Brachytherapy —Hype or Hope," *Bombay Hospital Journal* ( a publication of Bombay Hospital Institute of Medical Sciences), vol. 41 No.2, Apr. 1999 (5 pages) found at http://www.bhj.org/journal/1999_4102_apr99/sp_247.htm and cover sheet (2 pages) found at http://www.bhj.org/journal/1999_4102_apr99/contents.htm.

* cited by examiner

Primary Examiner—Paul J. Hirsch
(74) Attorney, Agent, or Firm—Blakely, Sokoloff, Taylor & Zafman LLP

(57) ABSTRACT

A method for delivering multiple doses of radiation to a target area of a vessel. The method includes delivering multiple radioisotopes to a target area of a vessel and allowing the radioisotopes to dwell in the target area for a period of time to deliver a predetermined and uniform radiation dose.

24 Claims, 6 Drawing Sheets

METHOD FOR RADIOACTIVE STENT DELIVERY

FIELD OF THE INVENTION

This invention relates to intraluminal vascular grafts, commonly referred to as stents, and more particularly concerns a method for delivery of radioactive stents.

BACKGROUND OF THE INVENTION

After a vessel has undergone treatment by percutaneous transluminal coronary angioplasty (PTCA), restenosis or narrowing of the vessel may occur. Two known contributors to restenosis are intimal hyperplasia, the formation of neointimal cells within the vessel, and vessel remodeling. Expandable stents are implanted within vessels in an effort to maintain vessel patency by preventing collapse and/or by impeding restenosis. Implantation of a stent is typically accomplished by mounting the stent on the inflatable portion of a balloon catheter, maneuvering the catheter through the vasculature so as to position the expandable stent at the desired location within a body lumen, and immediately inflating the balloon to expand the stent so as to engage the lumen wall. The stent returns to a predetermined shape in an expanded configuration allowing the balloon to be deflated and the catheter to be removed to complete the implantation procedure. However, restenosis after stent implantation may also occur.

Previously devised approaches to inhibit restenosis include intravascular radiation therapy also known as vascular brachytherapy. One such approach utilizes an expandable stent coated or imprinted with a radioactive isotope. The radioactive stent may be implanted in the same manner as a non-radioactive stent. Upon the immediate expansion of the radioactive stent to engage the vessel wall, the treated tissue receives a radiation dose for a time period defined by the radiation source chosen and its associated half-life. The delivered radiation dose results in localized cell kill at the treated site, thus inhibiting restenosis.

The radiation source may be either a gamma-emitting or a beta-emitting radioisotope. Radiation from a beta-emitting radioisotope diminishes rapidly with distance from the source thus delivering minimal energy at more than two millimeters. A beta-emitting radioisotope presents several advantages over a gamma-emitting radioisotope particularly in areas of safety of catheter laboratory personnel and ease of storage. On the other hand, a gamma-emitting radioisotope offers more penetration and can improve dose homogeneity.

Another approach to inhibit restenosis involves the exposure of the vasculature to an initial dose rate of high energy radiation followed by a second dose rate of lower energy radiation. Stents are imprinted with multiple radioisotopes in order to achieve the desired dosimetry. Multiple isotope radioactive stents are implanted in the vasculature in the same manner as single isotope radioactive stents and non-radioactive stents. This method includes positioning the stent in the target area and immediately deploying the stent to engage the vessel walls.

However, both single and multiple isotope radioactive stents have been associated with a "candy wrapper effect" caused by the inhibition of cell growth in the middle of the stent and neointimal cell proliferation at the distal and proximal ends of the stent. This "candy wrapper effect" may be caused by the delivery of a higher delivered dose in the middle of the stent resulting in cell kill in the middle region and delivery of a lower radiation dose at the ends of the stent which may inhibit, but to a lesser extent, neointimal cell formation.

Another approach for inhibiting restenosis involves delivering radiation using percutaneous intravascular catheters. A radiation source wire is inserted into a catheter lumen and the radiation source wire is advanced to the target region where the lesion is irradiated. After radiation therapy, the radiation source wire is withdrawn from the catheter. One of the problems associated with this method is ensuring the delivery of a circumferentially uniform dose to the target area. Since the radiation source wire is inserted through the catheter lumen, curvature in the catheter lumen or eccentricity at the target site can affect the uniformity of the dose delivered to the target area.

The above approaches for delivery of radiation potentially exhibit non-uniformity in the radiation dose delivered to the target area. Generally, a non-uniform radiation dose is characterized by uneven radiation doses delivered to the target area. An uneven radiation dose is typically further characterized by relatively high radiation doses also known as "hot spots" and relatively low radiation doses also known as "cold spots" being delivered within the target area.

A radioactive stent is typically constructed as a metal alloy mesh. The radioactive stent may be imprinted with a given radioisotope by bombardment of the stent with radioactive ions. Thus, the radioisotope is imprinted into the stent metal alloy. Once the stent is expanded, the mesh structure of the stent creates void areas adjacent to the metal alloy such that only approximately twenty percent of the vessel wall tissue in the target area is in contact with the metal alloy. Since radiation is attenuated with distance, tissue regions closer to the metal alloy receive a much higher dose of radiation than the tissue regions that are in the adjacent void areas. Thus, the tissue may receive a non-uniform pattern of radiation based upon the location of the expanded metal alloy mesh. The variation of absorbed radiation dose of the targeted tissue may contribute to the unfavorable vascular/cellular responses sometimes seen with radioactive stents.

Accordingly, a new method for uniform dose radioactive stent delivery is required.

SUMMARY OF THE INVENTION

The present invention provides a method for delivering multiple radioisotopes to a target area of a vessel and allowing the radioisotopes to dwell in the target area for a period of time to deliver a predetermined and uniform dose of radiation.

BRIEF DESCRIPTION OF THE DRAWINGS

The present invention is illustrated by way of example, and not limitation, in the figures of the accompanying drawings in which.

DETAILED DESCRIPTION OF THE INVENTION

The present invention is directed to a method for delivery of a radioactive stent. The present invention facilitates uniform radiation dosimetry during radioactive stent delivery. A desirable uniform radiation dosimetry is characterized by a more evenly distributed radiation exposure to a target area over time. The invention can be applied to devices for use in any body lumen or body cavity, such as the coronary arteries, the carotid arteries, the illiacs, the prostate, and other peripheral arteries and veins. The figures generally illustrate the methods used to deliver a radioactive stent in accordance with the present invention.

The present invention provides a method for delivering multiple doses of radiation to a target area of a vessel. The method includes delivering multiple radioisotopes to a target area of a vessel and allowing the radioisotopes to dwell in the target area for a period of time necessary to deliver a predetermined and uniform radiation dose. The combination of using multiple radioisotopes with a dwell period can result in a cumulative, and therefore higher and more evenly distributed radiation dose rate in the target area.

Figure 1:
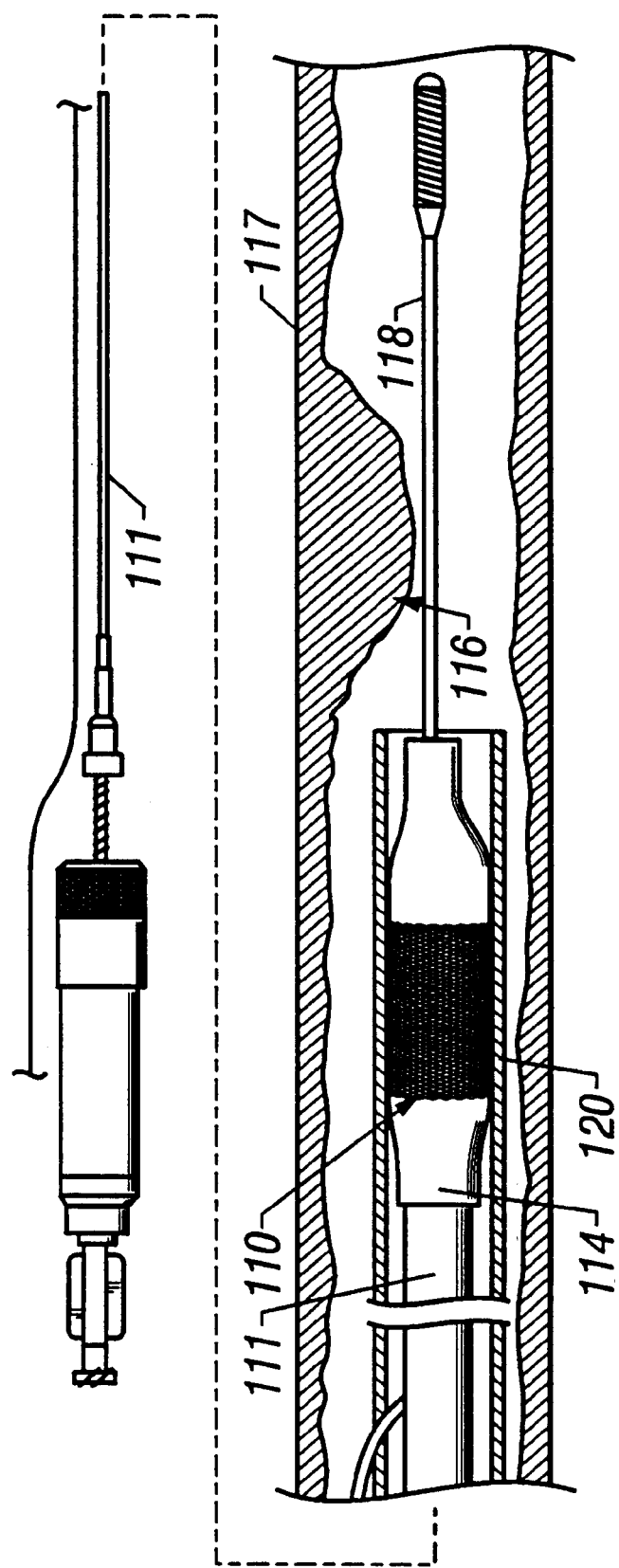
FIG. 1 is an elevational view, depicting a catheter delivery system including an enlarged, partial, cross-sectional view of the catheter delivery system within a vessel.

Referring to FIG. 1, a radioactive stent 110 is shown mounted on a delivery device 111. In one embodiment, a conventional balloon catheter known in the art can be adapted for use in practicing the invention. Typically, a guide wire 118 is initially inserted into a vessel 117. The end of the guide wire 118 is positioned distal to a target area 116. The delivery device 111 including the mounted radioactive stent 110 is inserted over the guide wire 118. Generally, the delivery device 111 is a flexible tube containing one or more lumens and one or more openings. The delivery device includes an expandable member 114 such as a balloon on the distal end of the delivery device 111. Typically, the radioactive stent 110 and expandable member 114 are encased within a retractable sheath 120 to help ensure that the mounted radioactive stent 110 remains properly positioned during insertion of the delivery device 111 through tortuous vasculature. Additionally, the retractable sheath 120 can shield the vasculature from exposure to radiation during insertion and positioning of the delivery device 111 in the target area 116.

Figure 2:
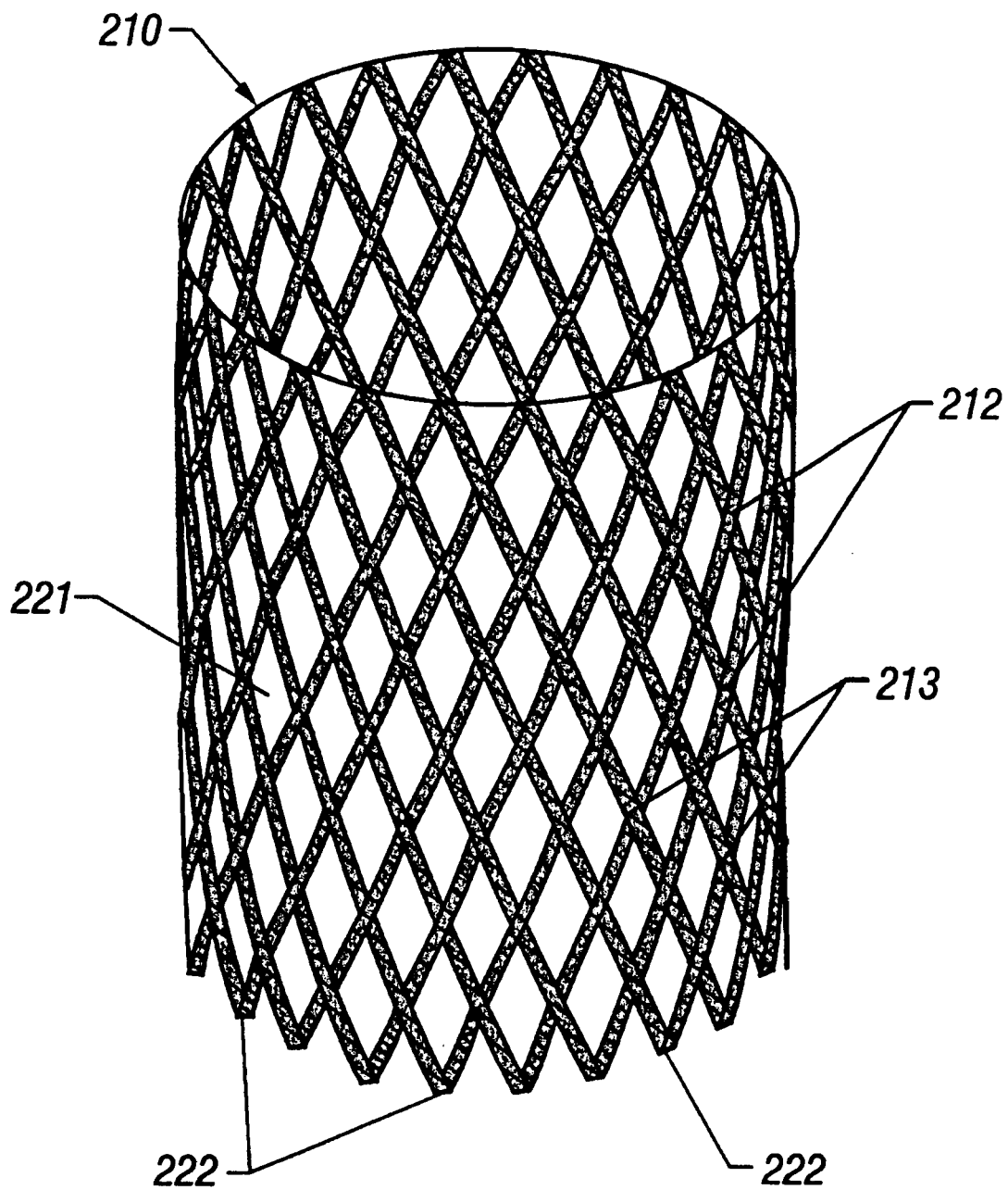
FIG. 2 is a perspective view, depicting a radioactive stent.

Referring to FIG. 2, an embodiment of a radioactive stent 210 is shown. The radioactive stent 210 includes a plurality of radially expandable elements 222. In its expanded or deployed state, the radioactive stent 210 has void areas 221 between the radially expandable elements 222. Any of a variety of radioactive stent configurations, including but not limited to interconnected independently expandable cylindrical elements or slotted tube-type designs may be delivered by practicing the invention.

In one embodiment, the radioactive stent 210 is imprinted with at least two radioisotopes. The first radioisotope 212, represented in FIG. 2 by a line pattern, is characterized by a higher energy and a shorter half-life. An example of a higher energy and a shorter half-life radioisotope is a positron-emitter radioisotope. The positron-emitter radioisotope is generally more penetrating than the second radioisotope. Preferably, the first radioisotope 212 includes a positron-emitter radioisotope such as Carbon-11 (C-11). A further example of an appropriate positron-emitter radioisotope is Fluorine-18 (F-18). Alternatively, the higher energy and shorter half-life radioisotope can be a gamma-emitter radioisotope such as Cobalt-57 (Co-57), Iridium-192 (Ir-192), Rhodium-106 (Rh-106), and Technetium-99m (Tc-99m). While specific examples of positron-emitter and gamma-emitter radioisotopes have been provided, the first radioisotope 212 can include any suitable positron-emitter or gamma-emitter radioisotope.

A second radioisotope 213, represented in FIG. 2 by a shaded pattern, is characterized by a lower energy and longer half-life as compared to the first radioisotope 212. Preferably, the second radioisotope 213 includes a beta-emitter radioisotope such as Phosphorus-32 (P-32). Further examples of appropriate beta-emitter radioisotopes include Phosphorus-33 (P-33), Rhenium-188 (Re-188), Tin-123 (Sn-123), Strontium-89 (Sr-89), Strontium-90 (Sr-90), Palladium-103 (Pd-103), Iodine-125 (I-125), Yttrium-90 (Y-90), and Xenon-133 (Xe-133). While specific examples of beta-emitter radioisotopes have been provided, the second radioisotope 213 can include any suitable beta-emitter radioisotope.

The radioisotopes may be imprinted on the surfaces of the stent by various methods known in the art. One example is ion beam implantation. Ion beam implantation includes converting an isotope to a gas phase. The gaseous isotope is ionized and injected into an ion beam accelerator where the ions are accelerated to a speed close to the speed of light. A stent is exposed to the accelerated ions and the isotope is imprinted onto the surfaces of the radially expandable elements 222 of the stent. Both the first radioisotope 212 and the second radioisotope 213 can be imprinted using ion beam implantation. In one embodiment, the stent is sequentially exposed to each of the ionized isotopes. The stent may require rotation and exposure to multiple ion beam cycles to overcome shadowing effects and to imprint an isotope over the entire surface of the stent. Thus, the first radioisotope 212 and the second radioisotope 213 are overlayed and imprinted upon the surfaces of the radially expandable elements 222 of the stent. While imprinting two radioisotopes has been described, a plurality of radioisotopes can be imprinted upon the surfaces of the stent.

Another method of imprinting the radioactive stent 210 with a first radioisotope 212 and a second radioisotope 213 includes plasma ion implantation. Plasma ion implantation includes use of a plasma chamber. Typically, a stent is placed in a plasma within a chamber and biased to high negative voltages. The high negative bias accelerates the isotope ions and implants the ions into the exposed surfaces of the radially expandable elements 222 of the stent.

Another method is coating the radially expandable elements 222 of the radioactive stent 210 with a first radioisotope 212 and a second radioisotope 213. Coatings may be applied using processes such as an anodic deposition process. While methods of imprinting and coating stents with radioisotopes have been described, alternate methods may be utilized.

Figure 3:
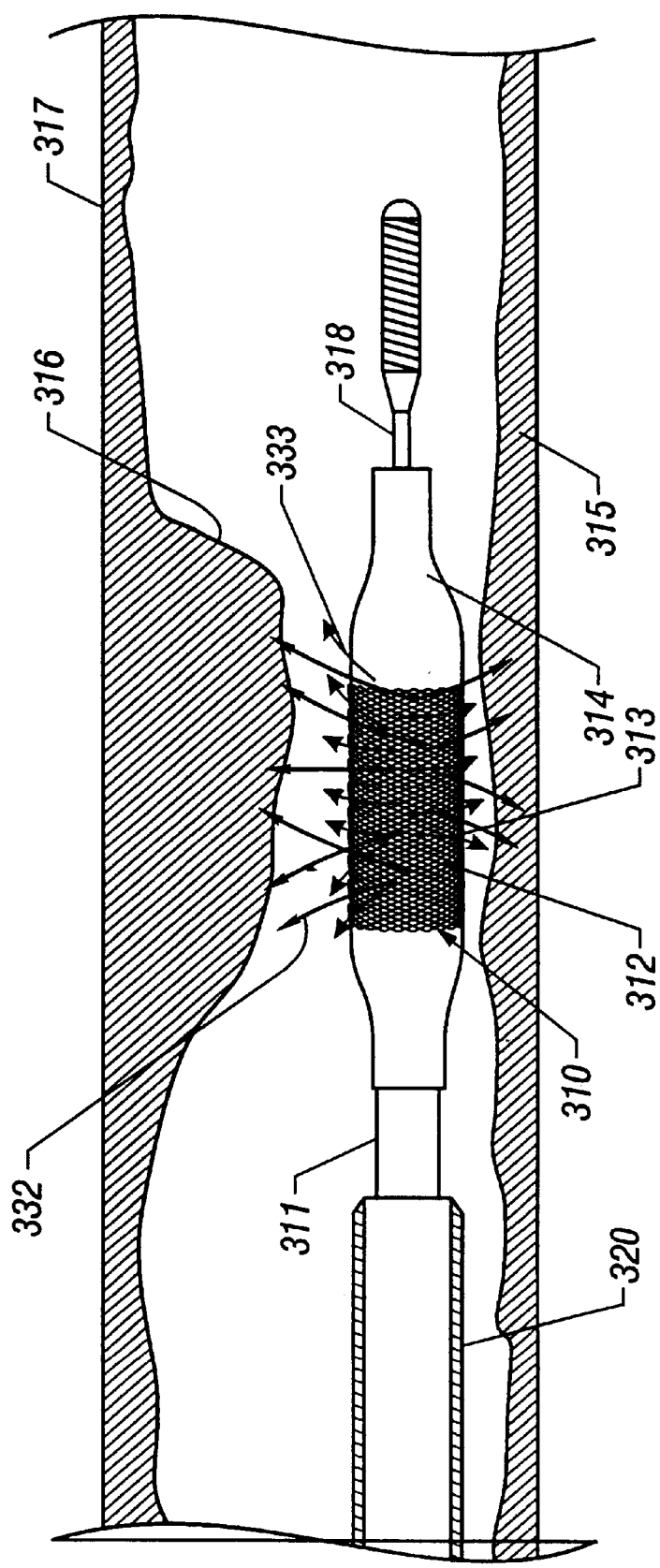
FIG. 3 is an elevational view, partially in section, depicting a catheter delivery system with an undeployed radioactive stent positioned in the target area in a vessel.

A method for delivery of the radioactive stent 310 is illustrated beginning in FIG. 3. The delivery device 311 and mounted radioactive stent 310 have been moved distally over the guide wire 318 to position the radioactive stent 310 in the target area 316 within the vessel 317. The retractable sheath 320 has been retracted proximal to the expandable member 314. The expandable member 314 is not inflated. The radioactive stent 310 imprinted with a first radioisotope 312 and a second radioisotope 313 is allowed to dwell in the undeployed state in the target area 316 for a period of time to deliver a predetermined dose of radiation. The dwell time can be based on the half-life of the first radioisotope 312.

In one embodiment, a radioactive stent 310 having a C-11 positron-emitter radioisotope with a half-life of approximately 20 minutes is allowed to dwell undeployed for a maximum of approximately 60 minutes. Typically, a time period of approximately 20 to 80 minutes can be used with a preferred maximum dwell period of 60 minutes. The desired clinical dose delivered is approximately 50 to 200 Gray (Gy). Preferably, the dwell period enables radial emission of radiation, represented in FIG. 3 by long arrows 332, from the C-11 positron-emitter radioisotope that penetrates the cell layer 315 within the target area 316 in locations distant from the radioactive stent 310.

The first radioisotope will continue to emit radiation indefinitely, but in ever decreasing amounts that can be considered negligible after a few to several half-lives. For example, a C-11 positron-emitter radioisotope has a half-life of 20 minutes. Therefore, after one hour or three half-lives, its activity will have decayed to about 12.5% of its initial value and after two hours or six half-lives, only about 1.6% of its original activity will remain.

Radiation from the second radioisotope 313, represented in FIG. 3 by short arrows 333, can penetrate the cell layer 315 in the target area 316 of the vessel 317 in radial locations within approximately 2 mm of the radioactive stent 310. As described in further detail below, the second radioisotope provides a lower energy and longer half-life compared to the first radioisotope. Because it is relatively lower energy, the second radioisotope exposes the target area 316 to radiation primarily when the radioactive stent 310 is expanded and has engaged the cell layer 315.

Figure 4:
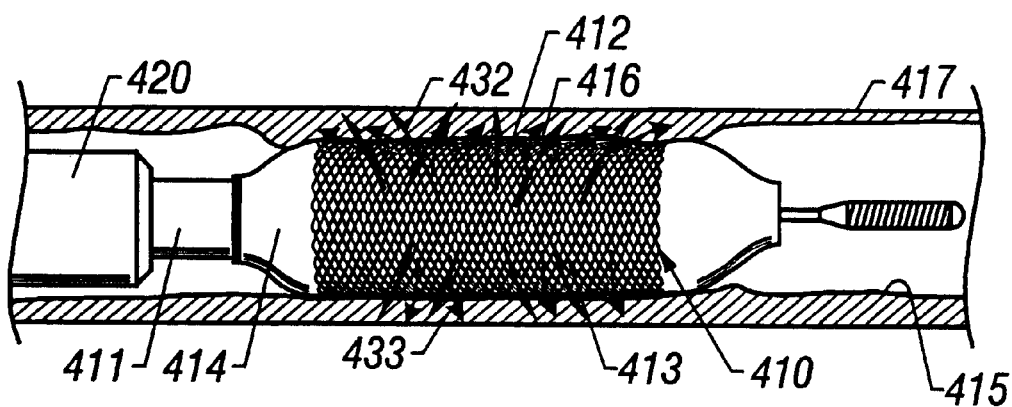
FIG. 4 is an elevational view, partially in section, depicting the catheter delivery system and radioactive stent of FIG. 3 in the process of expanding the radioactive stent.

In FIG. 4, an expanded radioactive stent 410 mounted on an expandable member 414 of a delivery device 411 is illustrated. The expandable member 414 is positioned in the target area 416 of the vessel 417. The retractable sheath 420 is proximal to the expandable member 414. Generally, the expandable member 414 of the delivery device 411 is inflated to high pressures using a suitable fluid such as saline. Typically, the expandable member 414 is inflated such that the radioactive stent 410 expands to a predetermined shape and engages the cell layer 415. The inflation of the expandable member 414 causes the target area 416 to be compressed against the outer wall of the vessel 417. The expandable member 414 may be inflated for a maximum time of approximately 420 minutes. The first radioisotope 412 will continue to emit radiation 432 as described above. In the expanded position, the radioactive stent 410 also emits radiation 433 from the second radioisotope 413 which can be absorbed by the cell layer 415 within the target area 416 of the vessel 417.

Figure 5:
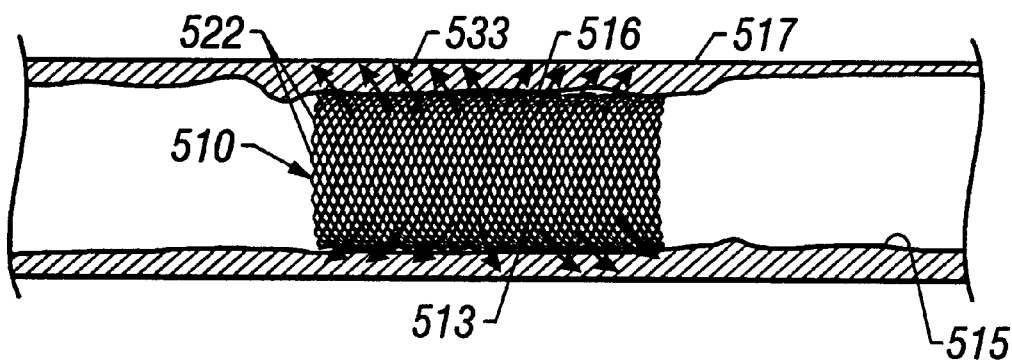
FIG. 5 is an elevational view, partially in section, depicting a deployed radioactive stent in the target area of a vessel.

FIG. 5 depicts a deployed radioactive stent 510 in the vessel 517. The radially expandable elements 522 of the radioactive stent 510 are engaged with the cell layer 515 and the target area 516 is compressed. The delivery device (not shown) has been withdrawn. The second radioisotope 513 preferably continues to emit radiation 533 until the emitted radiation becomes negligible. In one embodiment, the second radioisotope 513 is P-32 with a half-life of approximately 14 days.

A second method of delivering multiple radioisotopes includes a radioactive stent with a plurality of radially expandable elements imprinted with at least one radioisotope. The radioisotope is preferably a beta-emitter radioisotope such as P-32. The radioactive stent is mounted on a delivery device as described above, is introduced into a vessel, and is positioned in the target area of the vessel. After positioning the radioactive stent in the target area, the expandable member of the delivery device is immediately inflated using a radioactive medium such that the target area is compressed against the vessel wall.

The radioactive medium may include a radioactive fluid, a radioactive gas, or a radioactive slurry. The medium includes a radioisotope. Preferably, the radioisotope is Paladium-103 (Pd-103) with an approximate half-life of 17 days. The radioisotope included in the radioactive medium may be an x-ray-emitting, a gamma-emitting or a beta-emitting radioisotope because the radioactive medium contained within the expandable member is essentially in contact with the target area allowing greater penetration of radiation within the cell layer. Examples of suitable radioisotopes are Copper-61 (Cu-61), Selenium-73 (Se-73), Cobalt-55 (Co-55), Scandium-44 (Sc-44), Strontium (Sr-75), Krypton-77 (Kr-77), Gallium-66 (Ga-66), Gallium-68 (Ga-68), Gallium (Ga-72), Antimony-122 (Sb-122), Sodium-24 (Na-24), Silica-31 (Si-31), Bromine-76 (Br-76), Indium-110 (In-110), Holmium-166 (Ho-166), Iodine-125 (I-125), or Germanium-77 (Ge-77). The inflated expandable member can be allowed to dwell for a period of time to deliver a predetermined, uniform radiation dose. The dwell time is dependent on the radioisotope used in the radioactive medium. An approximate range of 5–20 minutes of dwell time is preferable with a desirable maximum dwell time of approximately 20 minutes. After the predetermined time elapses, the expandable member is deflated and the delivery device is withdrawn. The radioactive stent continues to deliver radiation until the emitted radiation is negligible.

Figure 6:
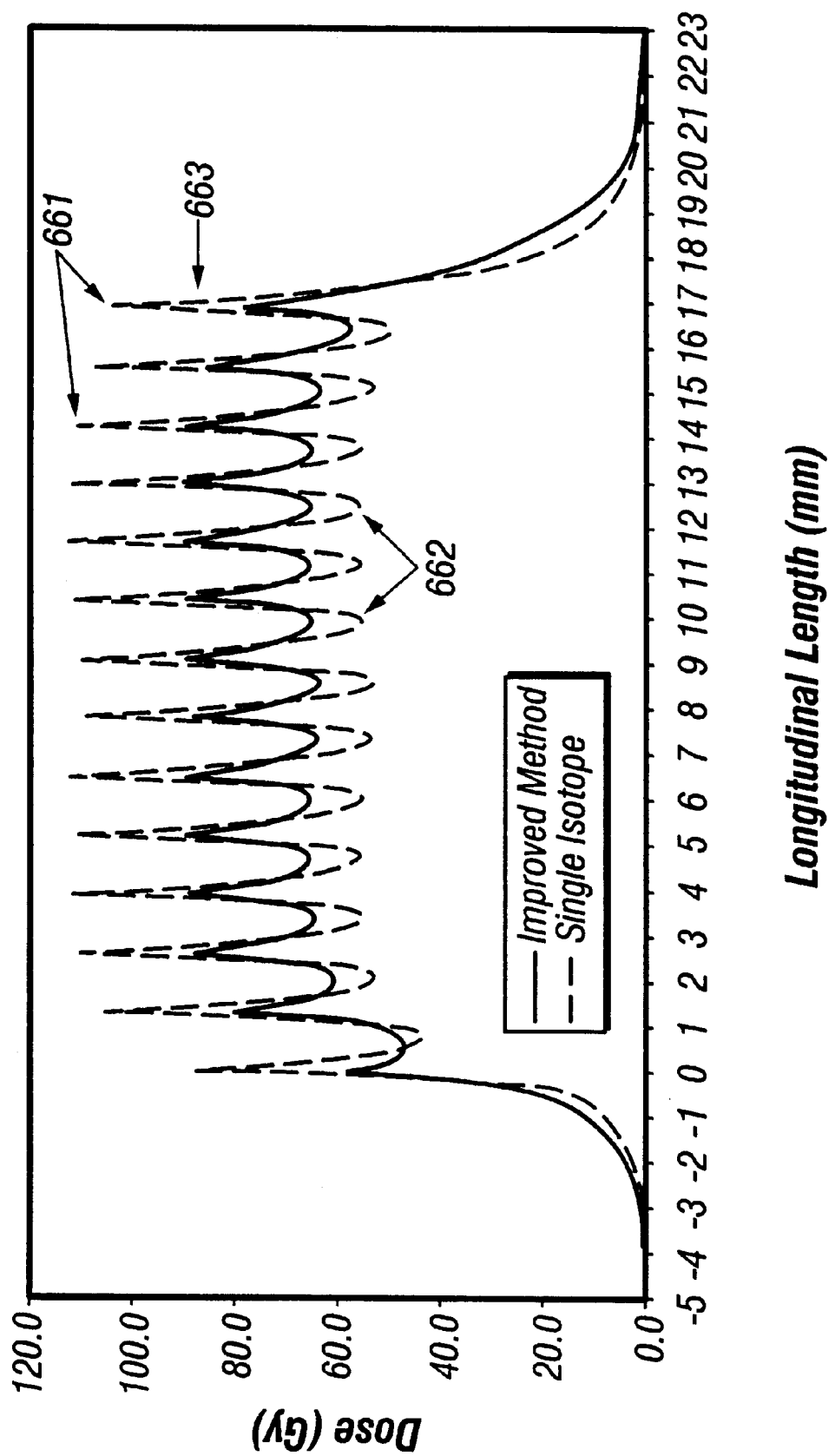
FIG. 6 is a comparative graphical illustration of an example of a dosimetry simulation of the present invention compared to prior art.
Figure 7:
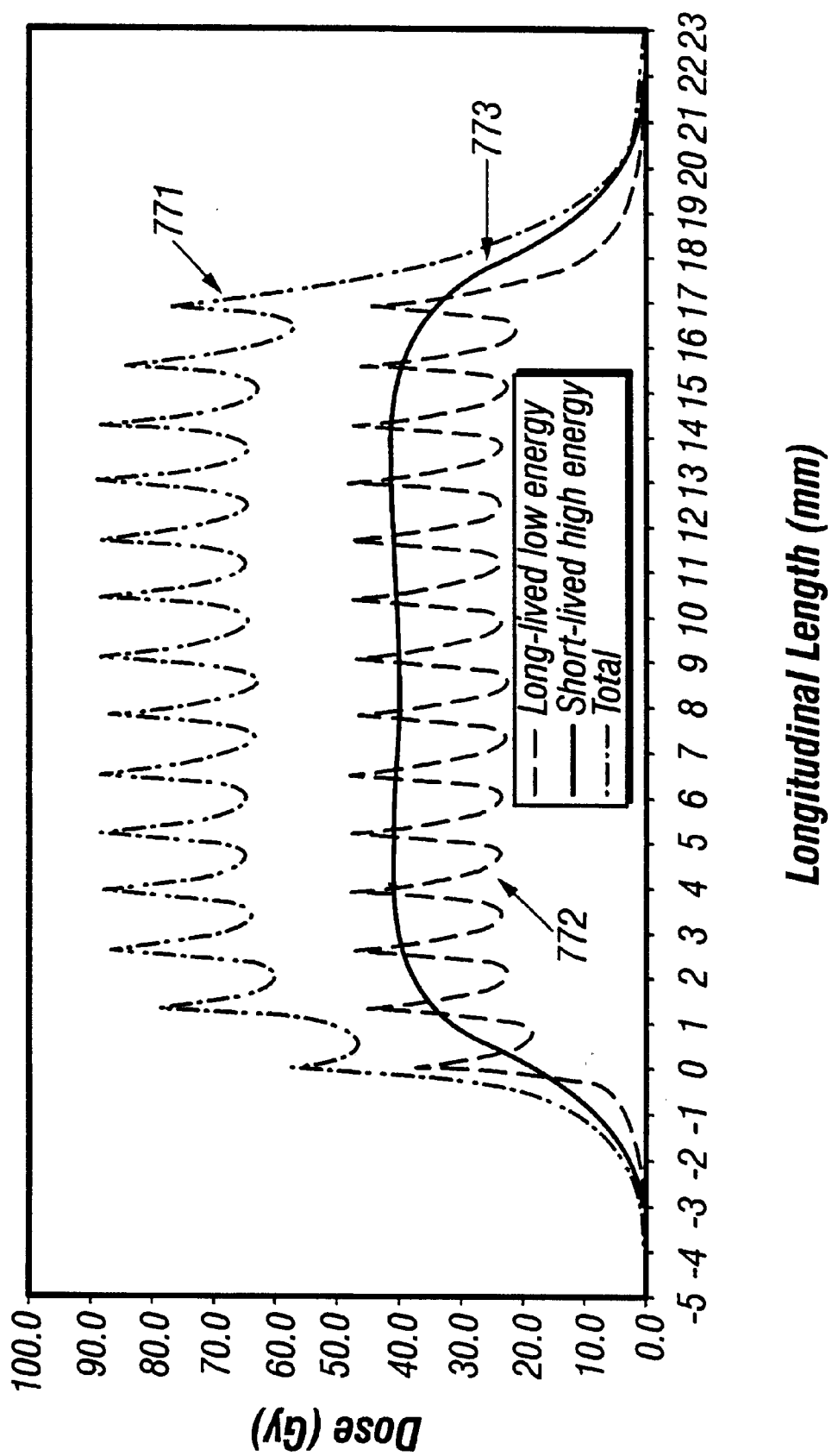
FIG. 7 is a graphical illustration of an example of a dosimetry simulation of the present invention.

Referring to graphical illustrations FIG. 6 and FIG. 7, an example of the effect of the methods of the present invention on the dosimetry profile is illustrated. FIG. 6 and FIG. 7 illustrate one representative example of the effect of one experimentation. FIG. 6 illustrates the effect of incorporating a dwell time while the radioactive stent is undeployed and positioned in the target area in accordance with the method of the present invention. As shown on the graph, the dosimetry profile is characterized by radiation dose peaks 661 and radiation dose valleys 662 corresponding to the effect of utilizing the mesh like structure of a stent for radiation delivery. Since radiation is attenuated with distance and is also subject to the inverse square law, the regions closest to the radially expandable elements 222 (FIG. 2) of the radioactive stent 210 receive a much higher dose rate of radiation than the regions facing void areas 221 of the radioactive stent 210 (FIG. 2). Thus, the dosimetry on the vessel wall presents a pattern of high doses also known as "hot spots" and low doses also known as "cold spots." The graph illustrates this effect with the peaks and valleys of a single isotope 663 showing that over the length of a radioactive stent, the radiation dose may vary from approximately 45–110 Gy.

On the other hand, a cellular layer located one to two millimeters deeper in the vessel wall and thus further from the radioactive stent will experience a reduction in the radiation dose variation due to the inverse square law since at this distance, no regions are very close to nor a great distance from the stent structure. Hence, the dose pattern is much more uniform, but also is weaker. One effect of the invention as shown in FIG. 6, takes advantage of this principle and reduces the radiation dose variation to approximately 50–90 Gy. This effect is attributed to the distance between the undeployed radioactive stent 310 and the target area 316 (FIG. 3), the use of multiple radioisotopes, and the incorporation of a dwell time necessary to ensure delivery of a predetermined radiation dose to the target area.

In FIG. 7, a cumulative effect of the two radioisotopes in the radioactive stent delivery methods is shown. In one embodiment, the short-lived high energy radioisotope 773 of the radioactive stent in the dwell stage of the method can deliver a relatively uniform radiation dose of approximately 40 Gy because during the dwell period, the radioisotope 773 is further away from the cell layer. The long-lived low energy radioisotope 772 can expose the target area to a radiation dose that can vary from approximately 20–50 Gy. Generally, the combination of the use of multiple radioisotopes in conjunction with the dwell stage of the delivery method results in a cumulative effect depicted as the Total line 771. As shown, the target area is exposed to a cumulative radiation dose that can range from approximately 50–90 Gy.

In the alternative embodiment, a radioisotope in the radioactive medium used to inflate the expandable member of the delivery system can deliver a uniform dose rate which is then combined with a lower energy long-lived radioisotope of the radioactive stent. The inflated expandable member can conform to the entire surface of the target area and therefore, can deliver a uniformly high dose of radiation unlike the variable radiation dose typically delivered by an expanded mesh structure of a radioactive stent.

While a particular embodiment of the invention has been illustrated and described, it will also be apparent to those skilled in the art that various modifications can be made without departing from the spirit and scope of the invention. Accordingly, it is not intended that the invention be limited except by the appended claims.

What is claimed is:

1. A method comprising:
   positioning an expandable radioactive stent including more than one radioisotope within a target area of a vessel;
   allowing the expandable radioactive stent to dwell undeployed within the vessel for a length of time necessary to expose the target area to a pre-determined radiation dose; and
   deploying the expandable radioactive stent within the vessel to cause the radioactive stent to engage a cell layer of the vessel.

2. The method of claim 1 wherein allowing the expandable radioactive stent to dwell undeployed within the vessel for a length of time includes determining a dwell time according to a half-life of the first radioisotope.

3. The method of claim 1 wherein allowing the expandable radioactive stent to dwell undeployed within the vessel for a length of time necessary to expose the target area to a pre-determined radiation dose further includes allowing the expandable stent to dwell for approximately 20 to approximately 80 minutes.

4. The method of claim 1 wherein positioning an expandable radioactive stent including more than one radioisotope includes positioning a first radioisotope and a second radioisotope, the first radioisotope having a higher energy and a shorter half-life than the second radioisotope.

5. The method of claim 4 wherein positioning a first radioisotope includes positioning a positron-emitter radioisotope.

6. The method of claim 5 wherein positioning a positron-emitter radioisotope includes positioning a positron-emitter radioisotope selected from the group consisting of C-11 and F-18.

7. The method of claim 4 wherein positioning a first radioisotope includes positioning a gamma-emitter radioisotope.

8. The method of claim 7 wherein positioning the gamma-emitter radioisotope includes positioning a gamma-emitter radioisotope selected from the group consisting of Ir-192, Co-57, Ir-192, Rh-106, and Tc-99m.

9. The method of claim 4 wherein positioning a second radioisotope includes positioning a beta-emitter radioisotope.

10. The method of claim 9 wherein positioning a beta-emitter radioisotope includes a beta-emitter radioisotope selected from the group consisting of P-32, P-33, Re-188, Sn-123, Sr-89, Sr-90, Pd-103, I-125, Y-90, and Xe-133.

11. A method comprising:
    positioning an expandable radioactive stent within a target area of a vessel,
    infusing a radioactive medium into an expandable member of a stent delivery system such that the expandable member is inflated and the expandable radioactive stent is deployed and engages a cell layer;
    allowing the expandable member to dwell inflated for a period of time necessary to deliver a predetermined dose to the target area of the vessel;
    deflating the expandable member; and
    withdrawing the stent delivery system.

12. The method of claim 11 wherein infusing the radioactive medium into an expandable member of a stent delivery system further includes infusing a solution containing a radioisotope.

13. The method of claim 11 wherein infusing the radioactive medium into an expandable member of a stent delivery system further includes infusing a gas containing a radioisotope.

14. The method of claim 11 wherein positioning the expandable radioactive stent within the target area of a vessel further includes positioning an expandable radioactive stent including a radioisotope selected from a group consisting of P-32, P-33, Re-188, Sn-123, Sr-89, Sr-90, Pd-103, I-125, Y-90, and Xe-133.

15. The method of claim 11 wherein allowing the expandable member to dwell inflated for a period of time necessary to deliver a predetermined dose includes allowing the expandable member to dwell inflated for a maximum of 20 minutes.

16. A method comprising:
    positioning a radioactive stent including a plurality of radioisotopes within a target area of a body lumen;
    delivering a dose of radiation to the target area by allowing the radioactive stent to dwell undeployed within the body lumen for a length of time necessary to deliver a predetermined radiation dose; and
    expanding the radioactive stent to engage the body lumen.

17. The method of claim 16 wherein delivering a dose of radiation to the target area includes delivering a first radioisotope and a second radioisotope, the first radioisotope having a higher energy and a shorter half-life than the second radioisotope.

18. The method of claim 16 wherein allowing the radioactive stent to dwell undeployed within the body lumen for a length of time further includes determining a length of time according to a half-life of a first radioisotope.

19. The method of claim 17 wherein delivering the first radioisotope includes delivering a positron-emitter radioisotope.

20. The method of claim 19 wherein delivering the positron-emitter radioisotope includes delivering a positron-emitter radioisotope selected from the group consisting of C-11 and F-18.

21. The method of claim 16 wherein delivering the first radioisotope includes delivering a gamma-emitter radioisotope.

22. The method of claim 21 wherein delivering the gamma-emitter isotope includes delivering a gamma-emitter radioisotope selected from the group consisting of Ir-192, Co-57, Ir-192, Rh-106, and Tc-99m.

23. The method of claim 17 wherein delivering a second radioisotope includes positioning a beta-emitter radioisotope.

24. The method of claim 23 wherein delivering a beta-emitter radioisotope includes delivering a beta emitting isotope selected from the group consisting of P-32, P-33, Re-188, Sn-123, Sr-89, Sr-90, Pd-103, I-125, Y-90, and Xe-133.

* * * * *

UNITED STATES PATENT AND TRADEMARK OFFICE
CERTIFICATE OF CORRECTION

PATENT NO.     : 6,524,232 B1
DATED          : February 25, 2003
INVENTOR(S)    : Tang et al.

It is certified that error appears in the above-identified patent and that said Letters Patent is hereby corrected as shown below:

<u>Title page,</u>
Item [56], References Cited, FOREIGN PATENT DOCUMENTS, please delete "DE     5059166      10/1991" and insert -- DE     4315002     8/1994 --.
OTHER PUBLICATIONS, "Fischell," reference please delete "θ" and insert -- β --.

Signed and Sealed this

Thirteenth Day of April, 2004

JON W. DUDAS
*Acting Director of the United States Patent and Trademark Office*